United States Patent
Yamamoto et al.

(10) Patent No.: US 6,610,014 B1
(45) Date of Patent: Aug. 26, 2003

(54) ULTRASONIC TOMOGRAPH WHICH SETS DOPPLER SAMPLE POINT FROM BLOOD FLOW INFORMATION, AND DOPPLER SAMPLE POINT SETTING METHOD

(75) Inventors: Masa Yamamoto, Nagareyama (JP); Masaru Suemune, Kashiwa (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 09/424,451

(22) PCT Filed: May 26, 1998

(86) PCT No.: PCT/JP98/02293
§ 371 (c)(1),
(2), (4) Date: Nov. 23, 1999

(87) PCT Pub. No.: WO98/53741
PCT Pub. Date: Dec. 3, 1998

(30) Foreign Application Priority Data

May 26, 1997 (JP) .............................. 9-135011

(51) Int. Cl.[7] .............................. A61B 8/06
(52) U.S. Cl. ..................... 600/453; 600/455
(58) Field of Search ............... 600/440–441, 600/443, 447, 453–456; 128/916

(56) References Cited

U.S. PATENT DOCUMENTS

| | | | | |
|---|---|---|---|---|
| 5,450,850 A | * | 9/1995 | Iinuma | 600/455 |
| 5,724,974 A | * | 3/1998 | Goodsell, Jr. et al. | 600/455 |
| 5,785,654 A | * | 7/1998 | Iinuma et al. | 600/441 |
| 6,048,314 A | * | 4/2000 | Nikom | 600/443 |
| 6,068,598 A | * | 5/2000 | Pan et al. | 600/453 |
| 6,322,509 B1 | * | 11/2001 | Pan et al. | 600/443 |
| 6,390,984 B1 | * | 5/2002 | Pan et al. | 600/453 |
| 6,423,006 B1 | * | 7/2002 | Banjanin | 600/453 |
| 6,464,641 B1 | * | 10/2002 | Pan et al. | 600/453 |

FOREIGN PATENT DOCUMENTS

| | | |
|---|---|---|
| JP | 5-63510 | 8/1993 |
| JP | 6-217975 | 8/1994 |

* cited by examiner

*Primary Examiner*—Francis J. Jaworski
(74) *Attorney, Agent, or Firm*—Antonelli, Terry, Stout & Kraus, LLP

(57) ABSTRACT

A Doppler sample point setting apparatus in a ultrasonic tomograph comprises a probe for transmitting and receiving ultrasonic waves to and from an object; a signal processing unit for causing the probe to transmit the ultrasonic waves, receiving and signal-processing ultrasonic reflected echo signals received by the probe, and outputting a ultrasonic tomogram, a bloodstream image and bloodstream information; a display unit for displaying the ultrasonic tomogram, the bloodstream image and the Doppler sample point; and a control unit for automatically setting the position of the Doppler sample point on the basis of the bloodstream information.

28 Claims, 15 Drawing Sheets

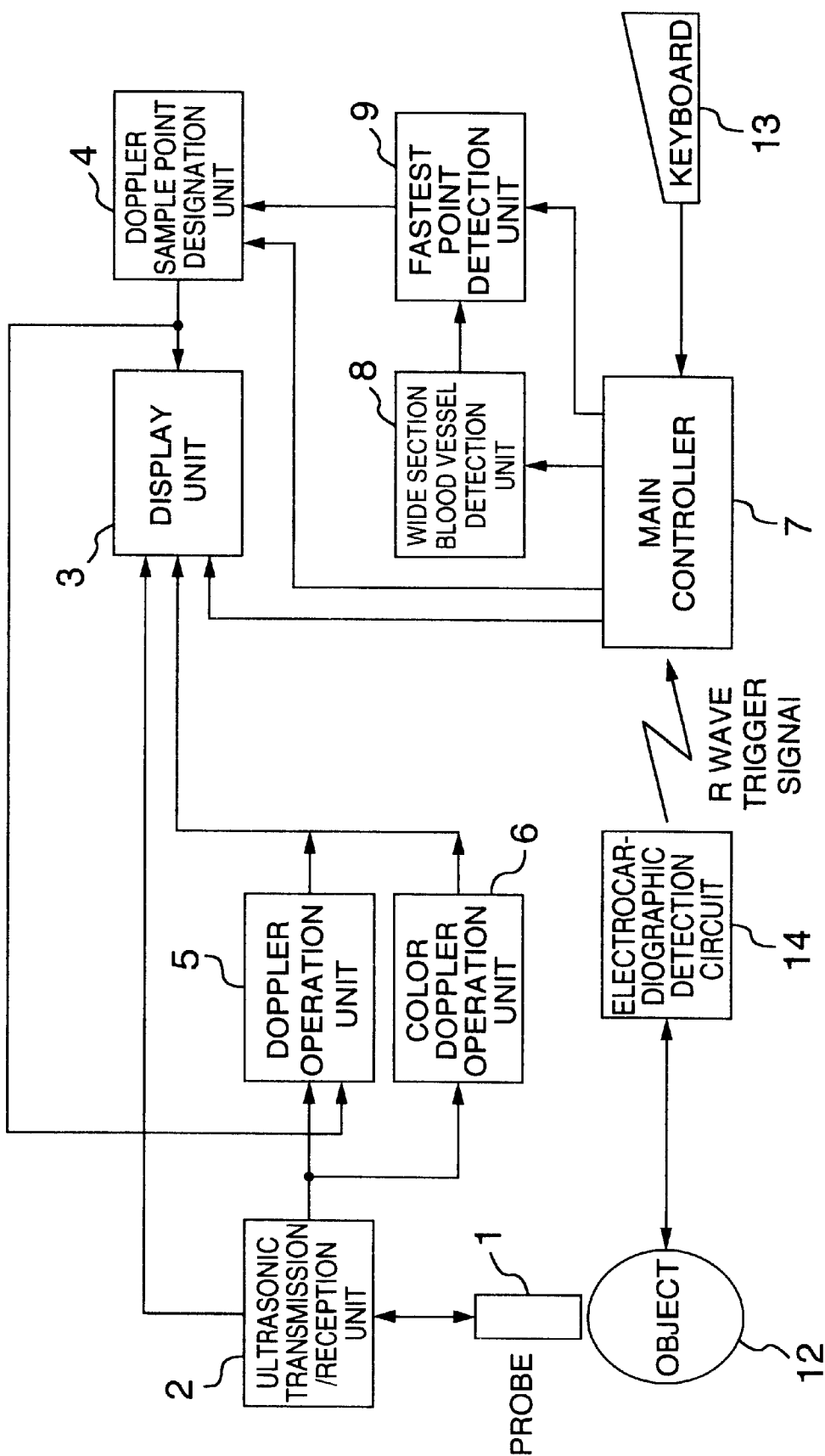

DISTRIBUTION EXAMPLE OF COLOR DISPLAY IN BLOOD VESSEL

ADDRESS OF ONE POINT INSIDE OBJECT
RANGE IS USED AS PARAMETER

CAROTID ARTERY

DOPPLER SAMPLE POINT

RANGE DESIGNATING CALIPER 1 IS MOVED BY TRACK BALL AND FIXED BY SET KEY

RANGE DESIGNATING CALIPER 2 IS MOVED BY TRACK BALL AND RANGE FRAME SIZE IS SET

RANGE DESIGNATION IS COMPLETED BY SET KEY

SAMPLE POINT AUTOMATIC SETTING

MOVEMENT — SAMPLE POINT RETRIEVING DIRECTION

SAMPLE POINT AUTOMATIC MOVEMENT

ULTRASONIC TOMOGRAPH WHICH SETS DOPPLER SAMPLE POINT FROM BLOOD FLOW INFORMATION, AND DOPPLER SAMPLE POINT SETTING METHOD

TECHNICAL FIELD

This invention relates to an apparatus, and a method, for setting a Doppler sample point in a ultrasonic tomograph. More particularly, this invention makes it possible to automatically set a desired Doppler sample point.

BACKGROUND ART

A conventional ultrasonic tomograph of this kind comprises a probe for transmitting and receiving ultrasonic waves into and from an object, a ultrasonic wave transmission/reception unit for transmitting the ultrasonic waves into a diagnostic portion of the object by driving the probe and inputting and processing reflected echo signals received by the probe, a display unit for inputting reception signals from the ultrasonic wave transmission/reception unit and displaying a ultrasonic tomogram of the diagnostic portion, a Doppler sample point designation unit for designating and displaying a Doppler sample point for a bloodstream portion of the ultrasonic tomogram displayed on the display unit, Doppler operation means for acquiring flow velocity information of the bloodstream at the Doppler sample point designated by the Doppler sample point designation unit, and a control circuit unit for controlling the operation of each of these constituent units. This ultrasonic tomograph achieves a Doppler function capable of observing the bloodstream flow velocity at an arbitrary point on the ultrasonic tomogram of the diagnostic portion and also a color flow mapping function of superposing the bloodstream movement, that includes the flowing direction of the bloodstream, the flow velocity and the change with time, at the diagnostic portion, with the ultrasonic tomogram, and displaying the movement in color. This technology is described, for example, in Navin C. Nanda, "Textbook of Color Doppler Echocardiography", p7–17 (1989).

In the conventional ultrasonic tomograph described above, the Doppler sample point is designated for the bloodstream portion of the ultrasonic tomogram displayed on the display unit by moving manually a Doppler sample setting mark to a position of a region of interest, at which the bloodstream exists, by moving means such as a track ball. The setting and diagnostic procedures in this case are as follows.

(1) The ultrasonic tomogram is observed.
(2) The movement of the bloodstream is observed by superposing color bloodstream information on the ultrasonic tomogram.
(3) When the Doppler sample point setting mark is set to the blood vessel the Doppler image of which is desired to be displayed, the Doppler image at that point is displayed, and the Doppler image is observed.

In this instance, the observation mode is switched in the procedure (3) to the Doppler image observation mode. However, the display position of the Doppler sample point setting mark exists at the center on the ultrasonic tomogram under the initial state and thereafter changes to the position that is displayed previously. Thereafter, an operator decides the region of interest of the Doppler image on the basis of the ultrasonic tomogram and the color bloodstream image, and then moves the position of the Doppler sample point by moving means such as the track ball. Even after the Doppler sample point is moved into the region of interest, the operator has to move and decide manually the position that is appropriate for the observation of the Doppler information inside the region of interest, at which the Doppler image can be displayed satisfactorily, while watching the ultrasonic tomogram, the color bloodstream image and the display condition of the Doppler image.

DISCLOSURE OF THE INVENTION

However, in such a conventional ultrasonic tomograph, the Doppler sample point for the bloodstream portion of the ultrasonic tomogram displayed on the display unit is designated by manually moving the Doppler point setting mark by using the moving means such as the track ball to the position at which the bloodstream exists on the region of interest, on the basis of the color bloodstream information displayed in superposition with the ultrasonic tomogram. Therefore, it needs time to move the Doppler sample point setting mark to the region of interest on the display image, or to set it to the position inside the region of interest at which the Doppler information can be observed satisfactorily.

In consideration of these problems, it is an object of the present invention to provide a ultrasonic tomograph capable of setting either automatically or semi-automatically the Doppler sample point to the bloodstream portion of the ultrasonic tomogram displayed as the image.

According to one aspect of the present invention, there are provided a sample point setting apparatus in a ultrasonic tomograph, and a method therefor, capable of setting a desired Doppler sample point, either automatically or semi-automatically, on the basis of bloodstream information, by transmitting and receiving ultrasonic waves to and from an object through a probe so as to form a ultrasonic tomogram, displaying it on a display unit, generating blood stream information by a Doppler operation unit, displaying it in superposition with the ultrasonic tomogram and moreover, designating a desired condition.

BRIEF DESCRIPTION OF DRAWINGS

FIG. 1 is a block diagram showing a ultrasonic tomograph according to one embodiment of the present invention.

BEST MODE FOR CARRYING OUT THE INVENTION

Figure 2A:
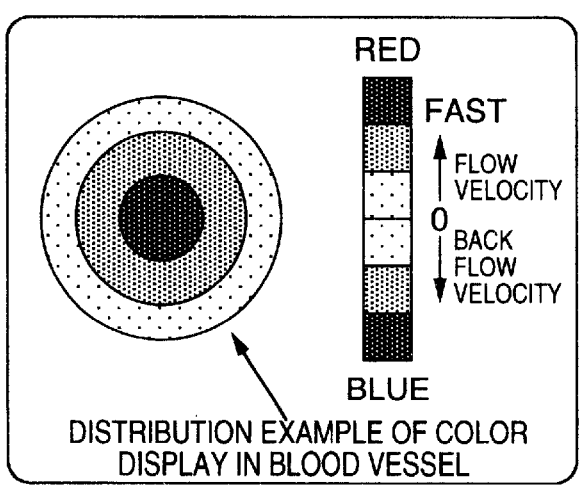
FIGS. 2A and 2B are an explanatory view of a color display distribution in a blood vessel and a schematic view showing a display example of a Doppler sample point setting mark.

Hereinafter, several embodiments of the present invention will be explained in detail with reference to the accompanying drawings.

FIG. 1 is a block diagram showing a ultrasonic tomograph according to an embodiment of the present invention. This ultrasonic tomograph transmits and receives ultrasonic waves into and from an object, acquires a ultrasonic tomogram of a diagnostic portion, displays the image, and accomplishes a Doppler function and a color flow mapping function. As depicted in FIG. 1, the ultrasonic tomograph comprises a probe 1, a ultrasonic wave transmission/reception unit 2, a display unit 3, a Doppler sample point designation unit 4, a Doppler operation unit 5, a color Doppler operation unit 6, a main controller 7, a wide section blood vessel detection unit 8 and a fastest point detection unit 9. The probe 1 transmits the ultrasonic waves to the diagnostic portion inside an object 12 and receives the reflected echoes from inside the object 12. The probe 1 has a built-in ultrasonic transducer as a generation source of the ultrasonic waves, for receiving the reflected echoes, though the transducer is omitted from the drawing. The ultrasonic wave transmission/reception unit 2 drives the probe 1 and lets it transmit the ultrasonic waves to the diagnostic portion inside the object 12, and inputs and processes the reflected echo signals received by the probe 1. The ultrasonic wave transmission/reception unit 2 has built-in pulse generator, reception amplifier and detection circuit, though they are omitted from the drawing. The display unit 3 inputs the reception signals outputted from the ultrasonic wave transmission/reception unit 2 and displays the ultrasonic tomogram of the diagnostic portion. The display unit 3 comprises, for example, an A/D converter for converting analog video signals to digital signals, an image memory for storing the digital image signals, a D/A converter for converting the digital image signals to analog video signals and a CRT for displaying the images from the analog video signals. Incidentally, in the example shown in FIG. 1, the ultrasonic tomogram displayed on the display unit 3 is the image that contains the bloodstream information.

The Doppler sample point designation unit 4 designates the Doppler sample point for the bloodstream portion of the ultrasonic tomogram displayed on the display unit 3, and displays the Doppler sample point setting mark on the display unit 3. This unit 4 is so constituted as to enable an operator to set manually the Doppler sample point. In other words, while the ultrasonic tomogram inclusive of the blood vessels is displayed on the display unit 3, the Doppler sample point is moved through an operation using a keyboard 13 connected to the main controller 7, such as a track ball, to the bloodstream portion as the region of interest. This position is displayed on the display unit 3 and at the same time, this position is instructed as the position for conducting the Doppler operation to the later-appearing Doppler operation unit 5.

The Doppler operation unit 5 executes an operation for acquiring the velocity information of the bloodstream for the Doppler sample point designated by the Doppler sample point designation unit 4 described above, and is well known. The Doppler operation unit 5 designates one specific ultrasonic beam on the ultrasonic tomogram displayed on the display unit 3, designates one or a plurality of Doppler sample points on this specific beam, determines the change with time of the bloodstream velocity at the Doppler sample point(s), and causes the display unit to display it as the Doppler image. The width of the time axis for displaying this Doppler image is generally a few seconds.

Figure 2B:
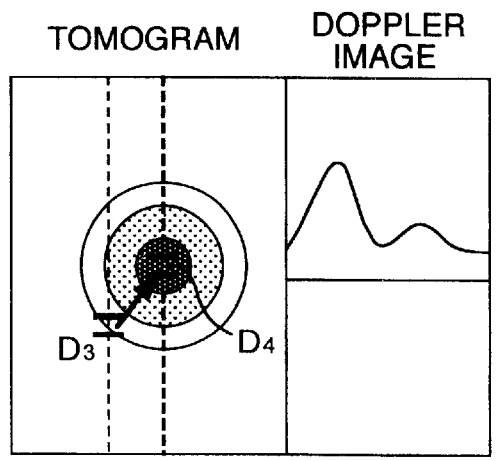

In order to form the ultrasonic tomogram, the color Doppler operation unit 6 constitutes color Doppler images by executing pseudo-coloring of the velocity information of all the pixel points for all the ultrasonic beams in such a manner as to correspond to each flow velocity, and displays it in superposition with the ultrasonic tomogram. Such a color Doppler operation unit is known as color flow mapping. For example, in one bloodstream portion, that is, in the blood vessel, the color Doppler operation unit 6 displays the portion having a higher flow velocity in one direction with a red color of a higher density, and displays the portion having a higher flow velocity in the opposite direction with a blue color having a higher density, as shown in FIG. 2A. Generally speaking, the closer to the center of the blood vessel, the higher becomes the flow velocity. Therefore, the color becomes denser at portions closer to the center. It is also possible to design this unit so that the color becomes brighter with a higher flow velocity, on the contrary. FIG. 2B shows on the right side the Doppler image at a Doppler sample point D4 when the Doppler sample point is moved from a point D3 to the bloodstream portion D4 having the highest flow velocity. The abscissa of the Doppler image represents the time, and the ordinate, the flow velocity. Vertical broken lines represent the ultrasonic beams used for the Doppler observation.

The main controller 7 serves as a control circuit unit for controlling the operation of each of the constituent elements described above, and includes a CPU (Central Processing Unit), for example. A keyboard 13 is connected to the main controller 7 for inputting various commands. When the Doppler sample point is determined on the color Doppler image constituted in synchronism with the heartbeats of the object 12, an electrocardiographic detection circuit 14 is provided for detecting the waveform of the electrocardiographic signals of the object 12. An R wave of the electrocardiographic wave obtained by this electrocardiographic detection circuit 14 is detected and is inputted as a trigger signal to the main controller 7.

The wide section blood vessel detection unit 8 distinguishes a large number of bloodstream portions on the basis of the Doppler image displayed on the display unit 3 and stipulates the bloodstream portion having the greatest sectional area among them. The fastest point detection unit 9 detects the bloodstream point having the highest flow velocity as a coordinate point on the display screen among the bloodstream portions of the maximum area that are detected by the wide section blood vessel detection unit 8, and sends it to the Doppler point designation unit 4. The Doppler sample point designation unit 4 designates the coordinate point as the Doppler sample point.

The wide section blood vessel detection unit 8 and the fastest point detection unit 9 operate independently of each other under the control of the main controller 7. The functions of these detection units 8 and 9 may be integrally incorporated into the main controller 7. The wide section blood vessel detection unit 8 and the fastest point detection unit 9 may be so constituted as to operate individually and independently of the main controller, respectively. In this case, when the wide section blood vessel detection unit 8 detects the bloodstream portion having the maximum area, an arbitrary point or a center point of this bloodstream portion is designated and the coordinates of this point are sent to the Doppler sample point designation point 4. When the fastest point detection unit 9 is so constituted as to operate independently, it detects the pixel having the highest flow velocity in all the images and sends its coordinate point to the Doppler sample point designation unit 4.

The wide section blood vessel detection unit 8 detects the blood vessel having the greatest blood vessel sectional area among a large number of blood vessels. When it is desired to set the Doppler sample point to the carotid artery, for example, the bloodstream portion having the greatest area may be retrieved because the carotid artery has generally a greater sectional area than other blood vessels. The wide section blood vessel detection unit 8 is used for such a case.

The individual operation of the wide section blood vessel detection unit 8 will be explained with reference to the flowchart shown in FIG. 3.

Figure 3:
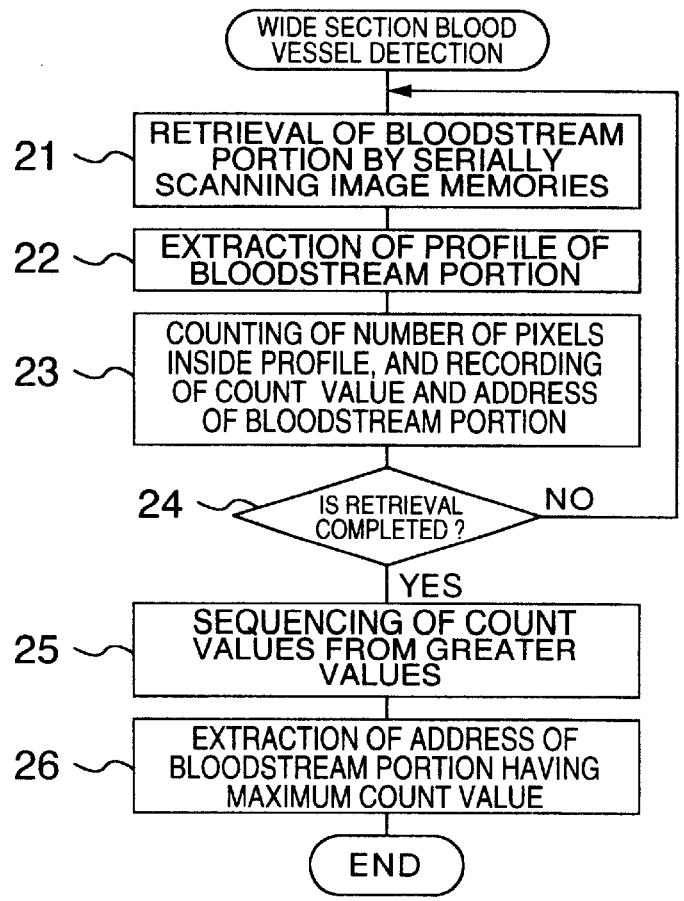
FIG. 3 is a flowchart showing the detection operation of a wide section blood vessel.

Referring to FIG. 3, since the color bloodstream information is stored in the image memories contained in the display unit 3, the image memories are checked serially from one of their ends in the pixel unit and retrieves the existing position of the bloodstream portion, in the step 21. In the next step 22, the profile of the bloodstream portion is defined for the bloodstream portion that is first retrieved during this retrieving operation, on the basis of the color bloodstream information. In other words, the boundary points between the pixel having the color bloodstream information and the pixel devoid of the color bloodstream information are serially detected, and this detecting operation is completed after returning to the start point. In consequence, the region in which the color bloodstream information exists consecutively is detected as one mass of the bloodstream portion. The extraction method of this profile is described in "Recognition and Learning", p106–109, published by Iwanami Shoten, May 20, 1991.

In the next step 23, the number of pixels existing inside the region encompassed by the profile is counted and is stored in the memory. The address of an arbitrary point inside the profile such as the point at which the bloodstream portion is first detected in the step 21 or the address on the image at the center point inside the profile, is stored in the memory.

Figure 4A:
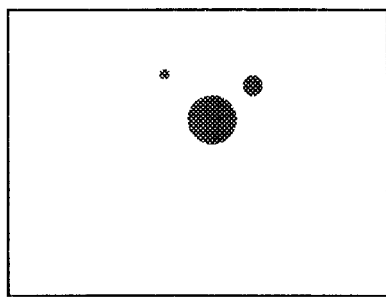
FIGS. 4A to 4D are explanatory views of the operation shown in FIG. 3.
Figure 4B:
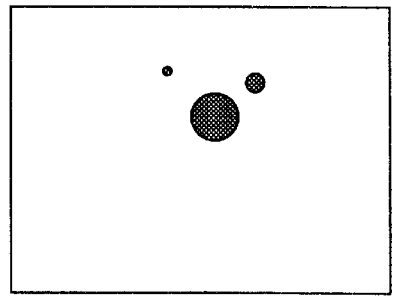
Figure 4C:
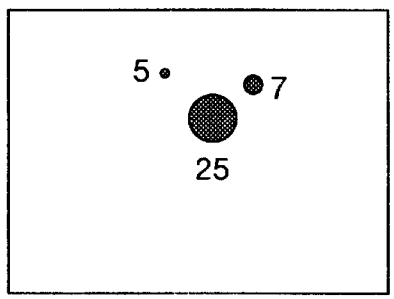

In the step 24, whether or not the retrieving operation reaches the end of the image memory is judged. If the judgement proves NO, the flow returns to the step 21, and the bloodstream portions are subsequently retrieved from the next pixel to the pixel, at which the bloodstream portion is detected finally, for the portions other than the region of the profile that is previously formed. If the judgement proves YES in the step 24, the bloodstream retrieval is completed for the entire screen of the display unit 3. In consequence, the bloodstream portion exhibits the image devoid of the profile as shown in FIG. 4A before the start of the operation shown in FIG. 2, but the profile is represented round the bloodstream portion after the operation is completed, as shown in FIG. 4B. In the step 23, the number of pixels representing the size of each bloodstream portion is recorded in the memory. The number of pixels may be represented as shown in FIG. 4C.

Figure 4D:
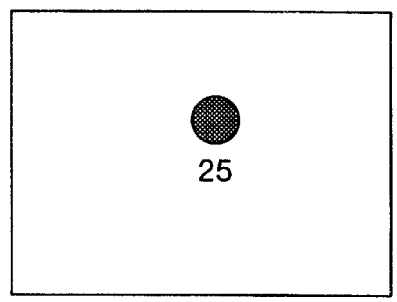

When the judgement proves YES in the step 24, the flow proceeds to the step 25. In this step 25, the count value determine by the step 23 and representing the area of each bloodstream portion is read out, and these bloodstream portions are sequenced from greater count values. In the case of the count values shown in FIG. 4C, for example, they are sequenced in the order of 25, 7 and 5. In the step 26, the bloodstream portion having the greatest pixel number is selected, and the address recorded in the step 23 is sent to the Doppler sample point designation unit 4, and only the bloodstream portion having the greatest area can be displayed as shown in FIG. 4D. The Doppler sample point setting mark is displayed at the recorded address portion. Thereafter, the required Doppler sample point can be adjusted manually by operating the track ball of the keyboard 13.

Next, explanation will be given on the case where the fastest point detection unit 9 operates individually.

Figure 5:
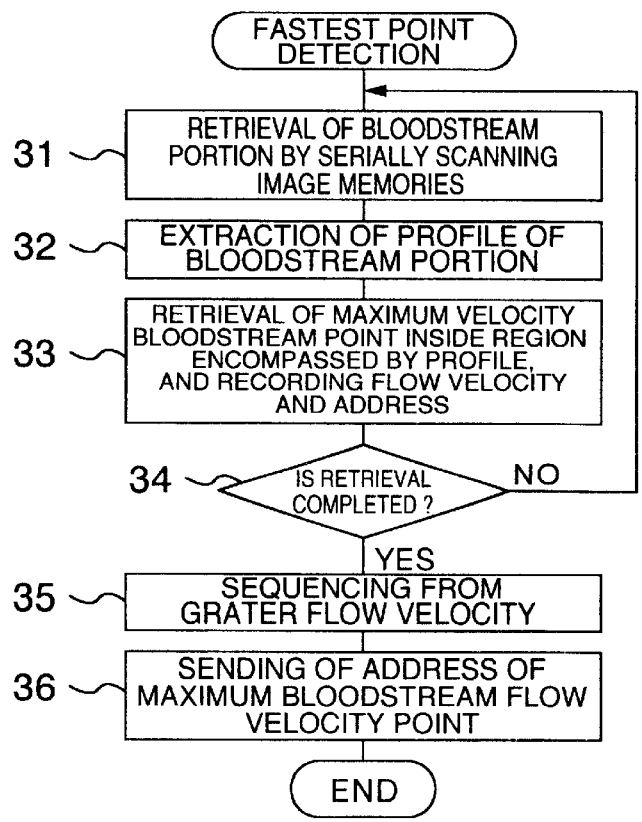
FIG. 5 is a flowchart showing the detection operation of the fastest point.

In FIG. 5, the operations of the steps 31 and 32 are the same operation as the steps 21 and 22 of FIG. 3. In the step 33, the flow velocity information is read out from the image memory for each pixel in the region encompassed by the profile, the pixel having the highest velocity in the flow velocity information is selected as the highest bloodstream point. The flow velocity and the address are stored in the memory, and then the flow proceeds to the step 34. The operation of the step 34 is the same as that of the step 24 of FIG. 3.

When the result of judgement proves YES in the step 34, the operation of the step 35 compares the bloodstream flow velocity of the highest velocity bloodstream point of each bloodstream portion determined by the step 33, and sequences the bloodstream points from the point having a higher flow velocity. In the step 36, the address of the bloodstream point having the highest order is sent to the Doppler sample point designation unit 4. As a result, the highest velocity bloodstream point is set as the Doppler sample point.

Figure 7A:
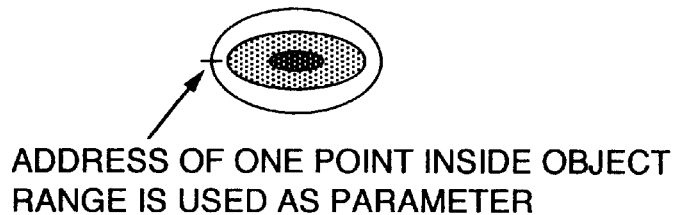
FIGS. 7A to 7D are explanatory views of the operation shown in FIG. 6.
Figure 7B:
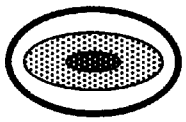
Figure 7C:
Figure 7D:
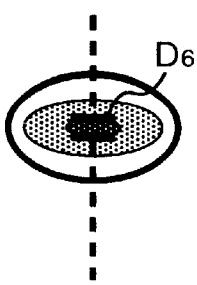

The fastest point detecting operation shown in FIG. 5 retrieves the highest velocity bloodstream point inside the whole screen. However, when the Doppler sample point setting mark is manually moved to a required bloodstream portion on the screen (the portion shown in FIG. 7A) in the step 41, the profile of the bloodstream portion is defined in the step 42 as shown in FIG. 7B. The operation of the step 43 retrieves the highest velocity bloodstream portion inside the bloodstream portion as shown in FIG. 7C, and in the step 44, the address of this point is sent to the Doppler sample point designation unit 4. As a result, the Doppler sample point setting mark is displayed at the highest velocity bloodstream portion so retrieved, as shown in FIG. 7D.

This embodiment can automatically set the Doppler sample point to the highest velocity bloodstream point by merely moving manually the Doppler sample point setting mark to a required bloodstream portion while the colored ultrasonic tomogram is being observed. Therefore, this embodiment can provide a ultrasonic tomograph having an extremely high operation factor.

Figure 6:
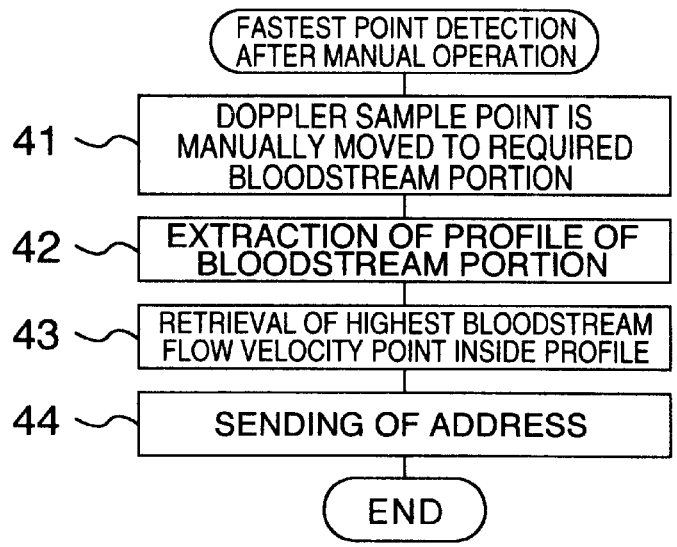
FIG. 6 is a flowchart showing the detection operation of the fastest point after a manual operation.
Figure 8:
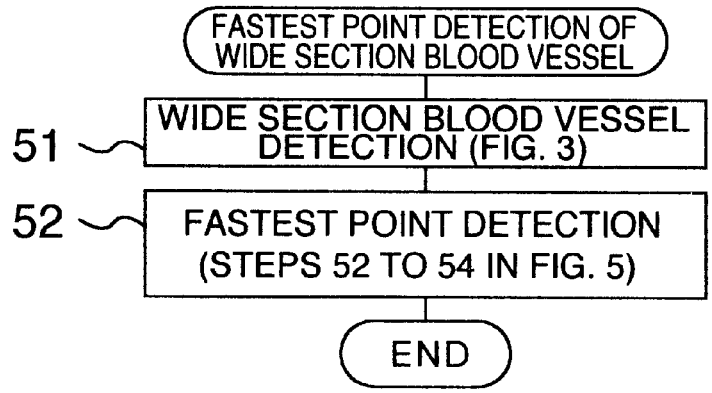
FIG. 8 is a flowchart showing the detection operation of the fastest point in succession to detection of a wide section blood vessel.

FIG. 8 is a flowchart, wherein the wide section blood vessel detection unit 8 first operates and retrieves the bloodstream portion having the greatest area as shown in FIG. 1. Then, the fastest point detection unit 9 operates and retrieves the highest velocity bloodstream point in the bloodstream portion having the greatest area. In FIG. 8, when the address of the greatest area bloodstream portion retrieved by the step 51 exists at the extreme left end as shown in FIG. 7A, the color bloodstream portion encompassed by the corresponding profile is extracted using the address of this one point as a parameter. Thereafter, the procedures are executed in the same way as the steps 42 to 44 of FIG. 6 (step 52).

Figure 9A:
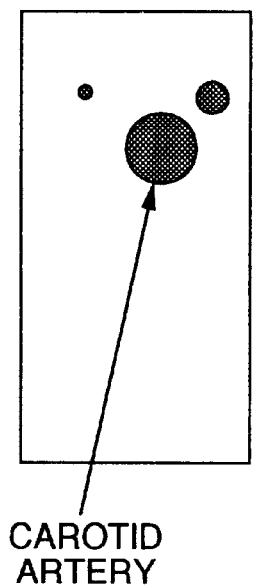
FIGS. 9A and 9B are explanatory views showing the operation of FIG. 8.
Figure 9B:
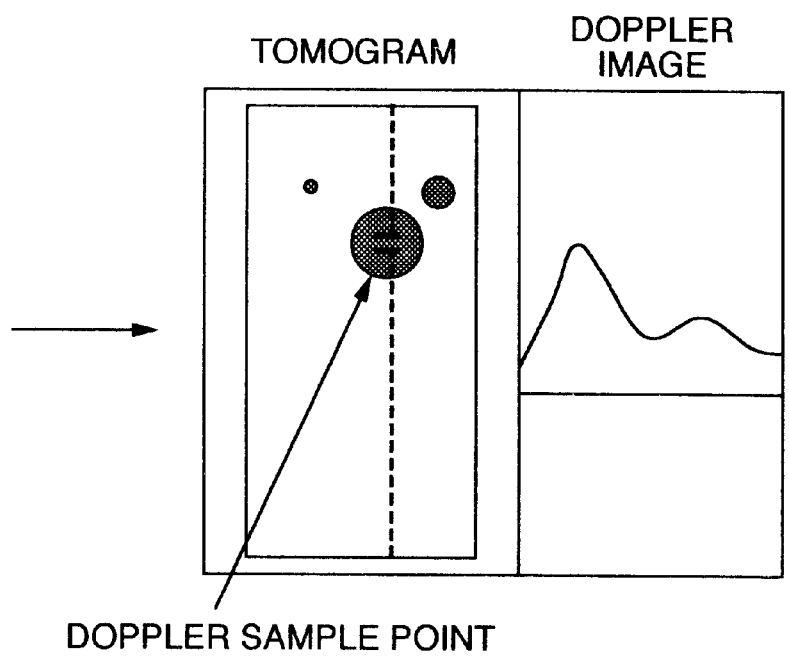

Therefore, if three, large, medium and small bloodstream portions exist as shown in FIG. 9A, for example, the bloodstream portion having the greatest sectional area, such as the carotid arteries, is retrieved, and the highest velocity bloodstream point in the carotid arteries is set as the Doppler sample point in the next step 52. As a result, the Doppler image of this set point is displayed.

Another embodiment of the present invention will be explained with reference to FIGS. 11A to 11C. When the bloodstream velocity of the valve mitralis portion in the heat is measured, the valve mitralis is interposed between the left ventricle and the left atrium and expands upon expansion of the left ventricle, generating the bloodstream. During shrinkage of the left ventricle, the left atrium is closed and does not generate the bloodstream. Therefore, measurement of the bloodstream of the valve mitralis must be executed only in the expansion period of the left ventricle.

Figure 11A:
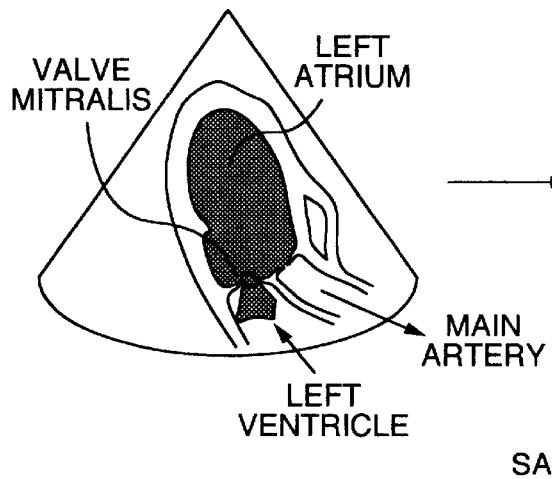
FIGS. 11A and 11B are explanatory views showing the operation of FIG. 10.
Figure 11B:
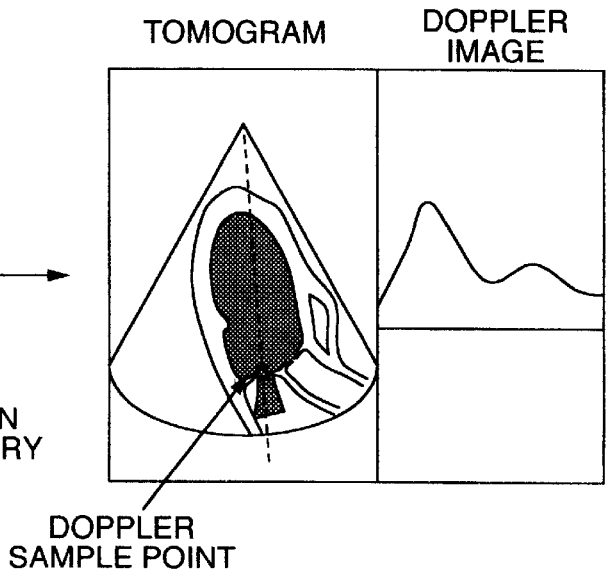
Figure 11C:
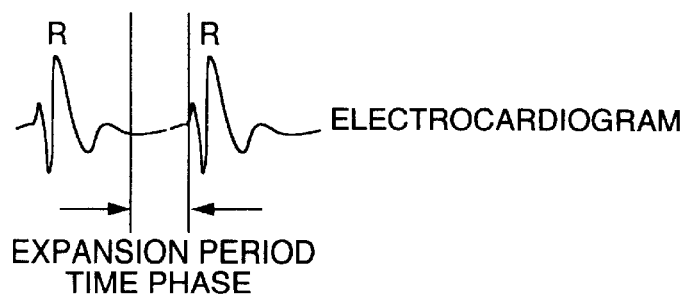

FIG. 11A is a sectional view of the left atrium of the heat in a direction of a longitudinal axis, and the valve mitralis is positioned at a portion communicating with the left ventricle. The electrocardiogram shown in FIG. 11C is detected from the object 12 using the electrocardiographic detection circuit 14. The main controller 7 sets the time phase of the expansion period of the left ventricle in synchronism with the R wave of the electrocardiogram and controls the apparatus so as to acquire the bloodstream information only in this time phase. The bloodstream flow velocity becomes high at the valve mitralis having a narrow passage in the expansion time phase of the left ventricle. Therefore, the bloodstream of the valve mitralis can be measured by retrieving the maximum bloodstream point in the expansion time phase of the left ventrcle.

Figure 10:
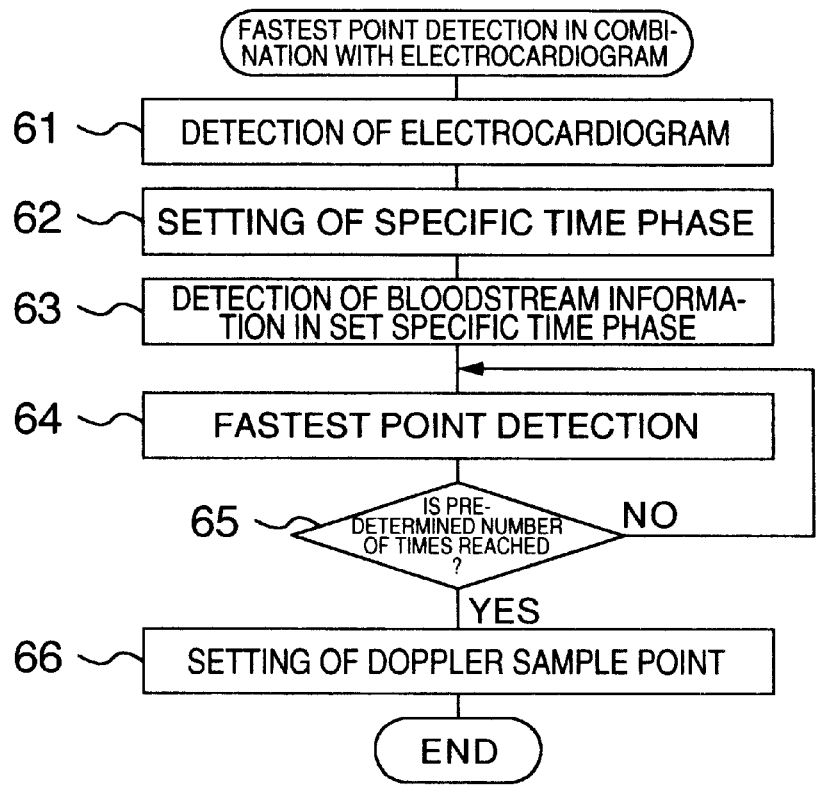
FIG. 10 is a flowchart showing the detection operation of the fastest point in combination with an electrocardiogram.

In FIG. 10, the electrocardiogram is detected from the electrocardiographic detection circuit 14 in the step 61, and the expansion time phase of the left ventricle is set on the basis of the R wave of the electrocardiogram. In the next step 63, the operation units 5 and 6 are controlled so that only the bloodstream information acquired in the expansion time phase can be processed by the Doppler operation unit 5 and by the color Doppler operation unit 6. In the step 64, the fastest point detection unit 9 is caused to execute the fastest point detection in accordance with the flow shown in FIG. 5. In the step 65, the detection unit 9 is caused to execute the fastest point detection a predetermined number of times, and in the next step 66, the Doppler sample point having the highest frequency or a mean Doppler sample point is calculated, and the result is sent as the Doppler sample point to the Doppler sample point designation unit 4. Consequently, the Doppler sample point is positioned to the valve mitralis portion as shown in FIG. 11B, and the Doppler image of this portion is displayed.

As described above, other valve portions in the heat can be measured by using conjointly the electrocardiogram, or the regurgitation of the blood-stream at the valve portion can be measured by the selection method of the time phase.

Incidentally, the bloodstream information of each bloodstream portion and analysis of the color image are always measured generally before the start of the Doppler mode. Therefore, as soon as the Doppler sample point is set, the Doppler image at the Doppler sample point can be displayed instantaneously.

Figure 12:
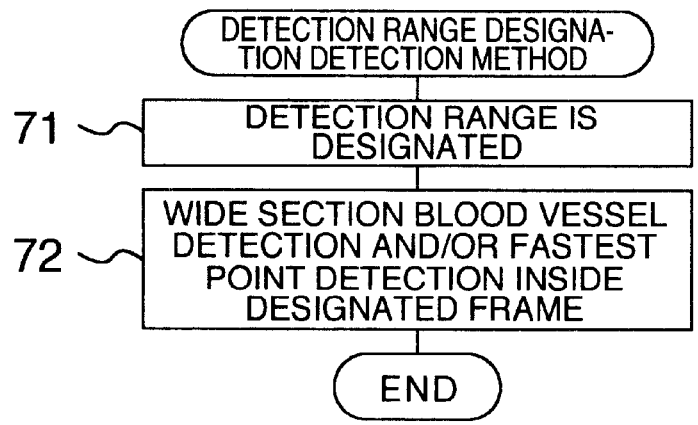
FIG. 12 is a flowchart showing the operation for designating a detection region.

When the Doppler sample point is automatically set, it is convenient in some cases to limit in advance the automatic setting range to a predetermined range and to execute automatic setting of the Doppler sample point only within such a range. FIG. 12 is a flowchart for executing such a procedure.

Figure 13A:
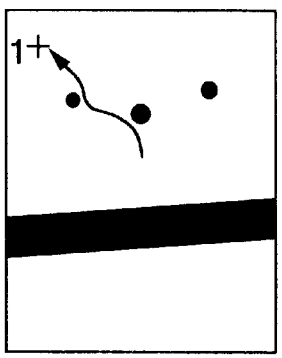
FIG. 13 is an explanatory view of the operation of FIG. 12.
Figure 13B:
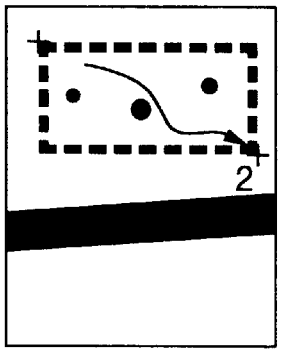
Figure 13C:
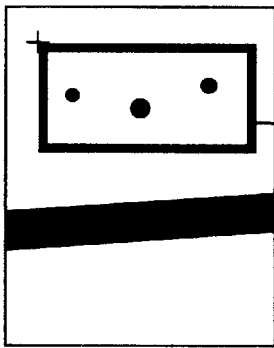
Figure 13D:
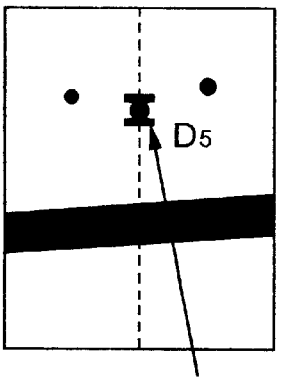

In FIG. 12, a region designation calipers+ are moved to the position 1 in FIG. 13A using the track ball provided to the keyboard 13 and is fixed to that position by a SET key, in the step 71. Next, when the calipers+ are moved to the position 2 in FIG. 13B using the track ball, the region designation frame size represented by broken lines is displayed. If it is a suitable size, the size is set by operating the SET key, and the region designation frame R1 is set as shown in FIG. 13C. In the step 72, the wide section blood vessel detection shown in FIG. 3, the fastest point detection shown in FIG. 5, the fastest point detection of the wide section blood vessel shown in FIG. 8 or the fastest point detection in combination with the electrocardiogram shown in FIG. 10, is executed inside the designated frame R1. As a result, the Doppler sample point D5 is set as shown in FIG. 13D.

Figure 14:
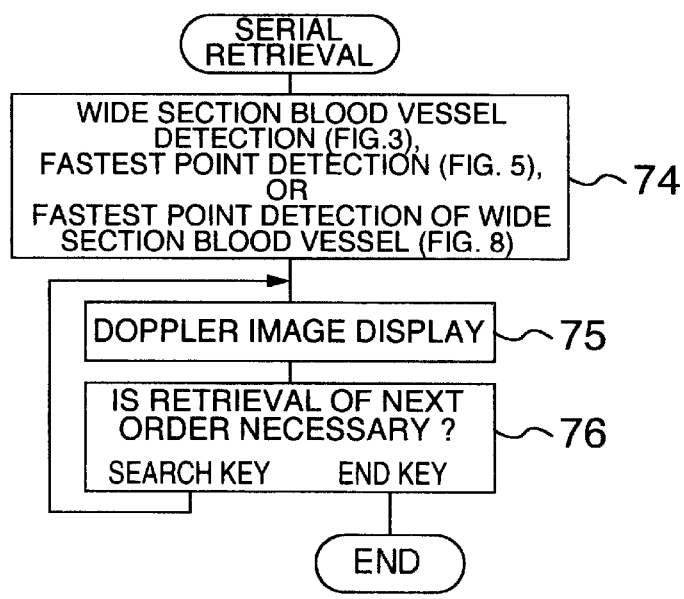
FIGS. 14 and 15 are flowcharts showing the operation for serially changing the Doppler sample point by a key operation.

FIG. 14 is a flowchart showing the procedure of the operation for moving serially the Doppler sample point in the direction in accordance with the sequence of the bloodstream portions having a greater sectional area, or in accordance with the bloodstream portions having a greater flow velocity, towards the bloodstream portions having smaller values.

In FIG. 14, the wide section blood vessel detection shown in FIG. 3, the fastest point detection shown in FIG. 5, the fastest point detection of the wide section blood vessel shown in FIG. 8 or the preliminary setting of the detection region designation frame shown in FIG. 12 is executed in the step 74. In the step 75, the Doppler image is displayed for the Doppler sample point that is set at first. If the retrieval of the subsequent sequence is necessary, a search key is pushed and then the flow returns to the step 75, so that the Doppler sample point of the next sequence is designated and the Doppler image is displayed. If retrieval is not necessary in the step 76, an END key is pushed and the procedure is completed. These sequences are determined in accordance with the one set by the step 25 in FIG. 3 or the step 35 in FIG. 5.

Figure 15:
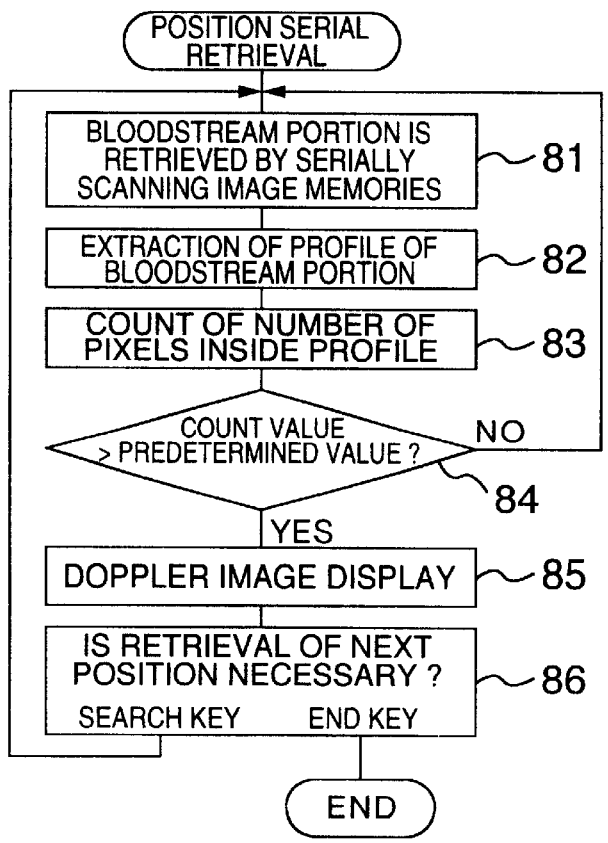

FIG. 15 is a flowchart showing the operation procedure for serially moving the position of the Doppler sample point for each bloodstream portion so that these sample points can be observed, respectively.

In FIG. 15, the steps 81 and 82 are the same as the steps 21 and 22 in FIG. 3. In the step 83, the number of pixels inside the profiles is counted. In the step 84, the bloodstream portion is estimated as an unnecessary noise if the count value is smaller than a predetermined value, and this bloodstream portion is neglected. The flow then returns to the step 81 so as to retrieve the next bloodstream portion. If the result proves YES in the step 84, the Doppler sample point for the bloodstream portion is displayed in the step 85 and the Doppler image is displayed. In this case, movement to the bloodstream point that is more necessary can be effected manually. The operation of the step 86 is the same as that of the step 76 shown in FIG. 14.

The description given above explains the various setting methods of the Doppler sample point. Next, setting of the initial display position of the Doppler sample point will be explained with reference to the flowchart of FIG. 16.

Figure 16:
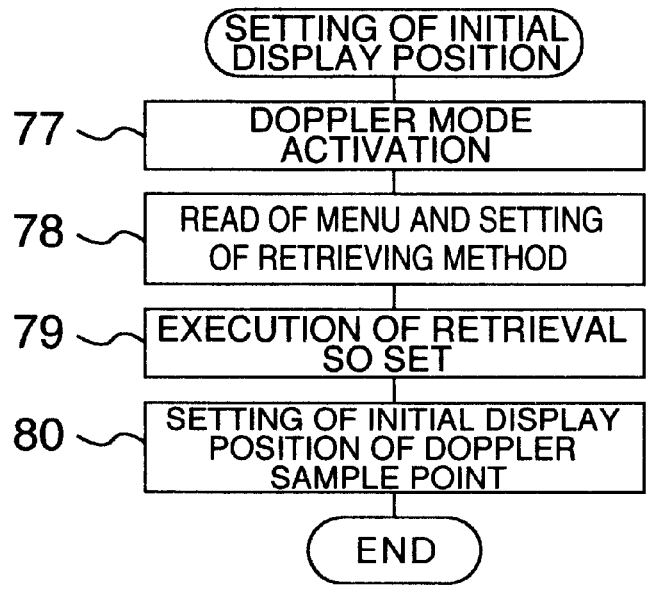
FIG. 16 is a flowchart showing the operation for setting an initial display position of the Doppler sample point.

In FIG. 16, the Doppler mode is activated by operating the keyboard 13 (step 77) in order to observe the Doppler image in the ultrasonic tomogram by the ultrasonic tomograph. In the next step 78, the menu of the Doppler sample point detection method is read out and any one of them is set. The Doppler sample point retrieval method includes means such as wide section blood vessel detection, the fastest point detection, the fastest point detection of the wide section blood vessel, the fastest point detection in combination with the electrocardiogram, detection region designation detection, and so forth. In the step 78, one of these methods is selected. The Doppler sample point detection method so set is executed in the step 79, and the initial display position of the Doppler sample point is set in the step 80.

After the initial display position of the Doppler sample point is set, the Doppler sample points can be changed one after another by using the serial retrieval method or the position serial retrieval method as explained with reference to FIGS. 14 and 15. Otherwise, the setting mark can be moved manually to the Doppler sample point of interest. In this case, after the setting mark is moved manually to the bloodstream portion of interest, the Doppler sample point can be set automatically to the fastest bloodstream point.

When the operator starts moving the Doppler sample point setting mark in the existing direction of the bloodstream portion of interest, the bloodstream portions existing in this direction can be automatically retrieved and the desired Doppler sample point can be set. Hereinafter, such a retrieval method will be explained with reference to FIG. 17.

Figure 17:
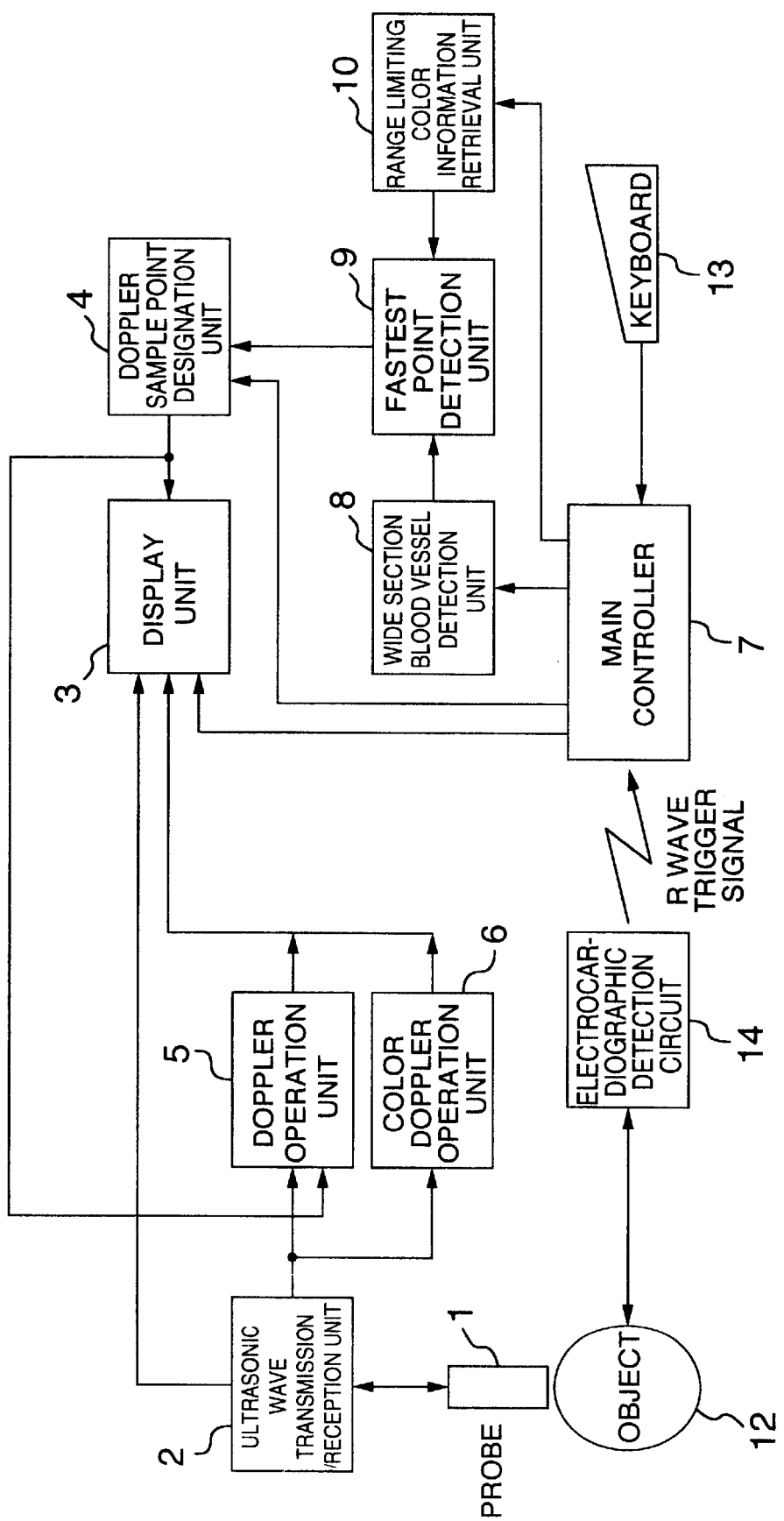
FIG. 17 is a block diagram showing another embodiment according to the present invention.

FIG. 17 is a block diagram showing a ultrasonic tomograph according to another embodiment of the present invention. The ultrasonic tomograph in this embodiment is constituted by connecting a range limiting color information retrieval unit 10 to the fastest point detection unit 9 in the ultrasonic tomograph in the embodiment shown in FIG. 1. The range limiting color information retrieval unit 10 senses the moving direction of the Doppler sample point when its movement is started in order to designate the Doppler sample point by the Doppler sample point designation unit 4. This retrieval unit 10 also functions as moving direction bloodstream detection means for detecting the presence/absence of the color bloodstream information in this moving direction. This retrieval unit 10 is used when the sample point in the moving direction of the track ball of the keyboard 13 connected to the main controller 7, for example, is detected.

Figure 18:
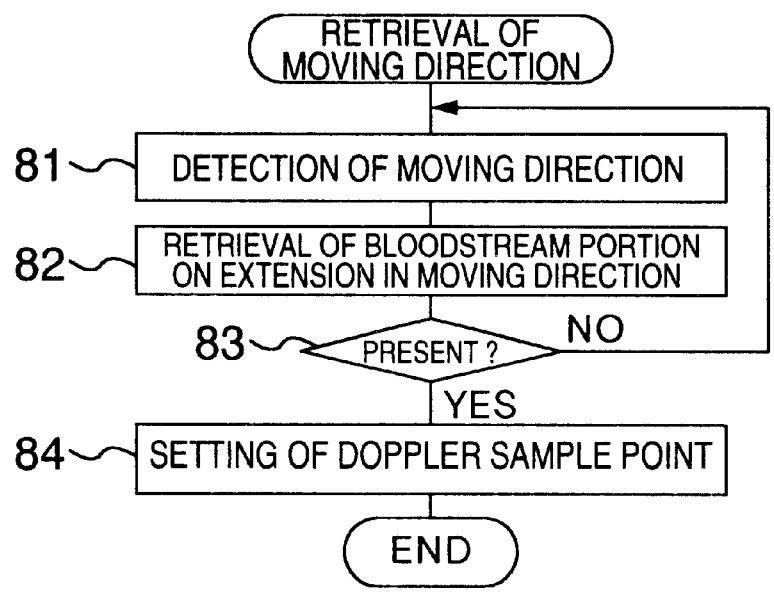
FIG. 18 is a flowchart showing the operating for retrieving the bloodstream portion in a moving direction of the Doppler sample point.
Figure 19A:
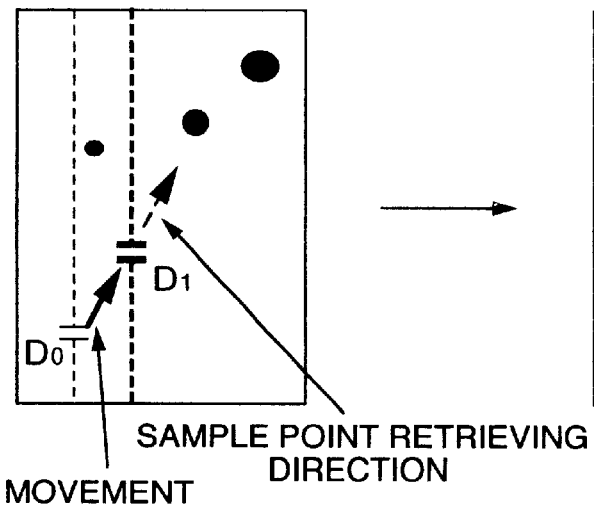
FIGS. 19A and 19B are explanatory views of the operation of FIG. 18.
Figure 19B:
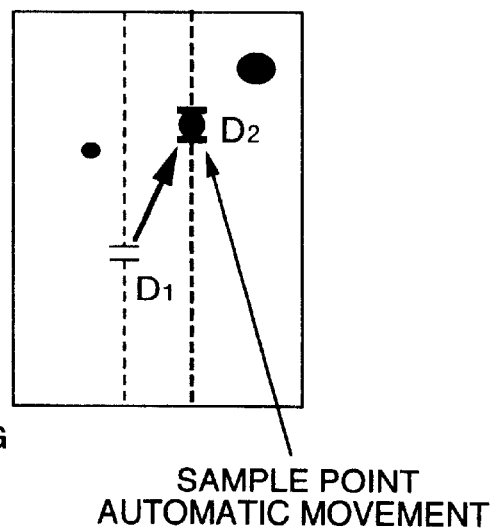

FIG. 18 shows the operation flow of a range limiting color information retrieval unit 10. When the Doppler sample point is moved from the position $D_0$ to $D_1$ by the track ball of the keyboard 13 as shown in FIG. 19A, the moving direction is detected in the step 81. In the next step 82, the bloodstream portion is retrieved in the extension of the moving direction. If the bloodstream portion is judged as existing in the step 83, the bloodstream portion is set as the Doppler sample point in the step 84 as represented by the point $D_2$ in FIG. 19B. If it does not exist, the flow returns to the step 81, and retrieval is similarly made from the position $D_1$ for the next movement. Incidentally, the sample point may be set in the step 84 by executing the fastest point detection.

Another example of the range limiting color information retrieval unit 10 shown in FIG. 17 will be explained with reference to the flowchart shown in FIG. 20.

Figure 20:
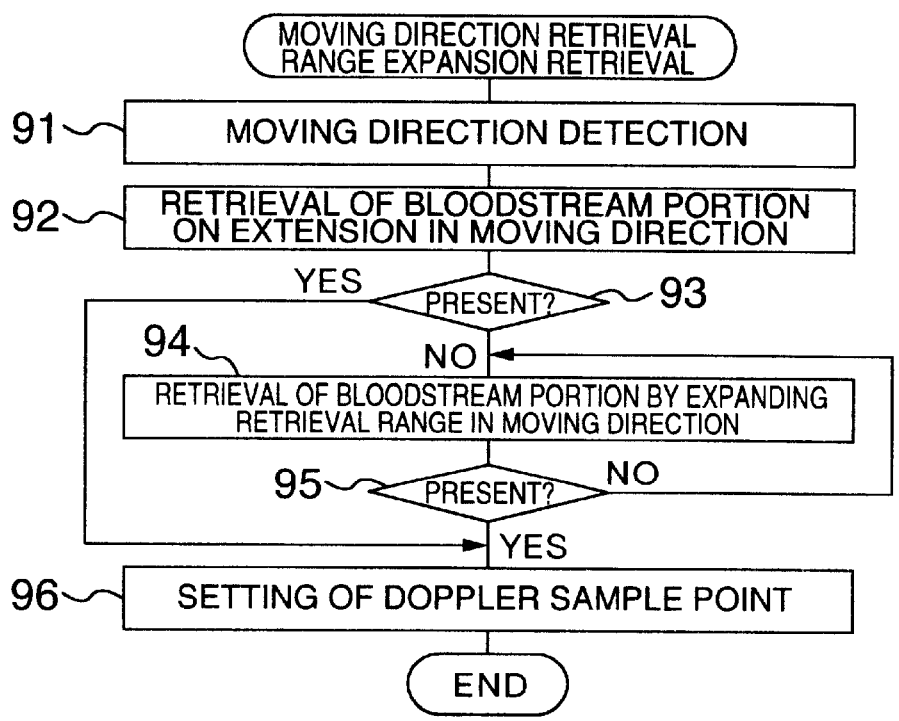
FIG. 20 is a flowchart showing an extended retrieving operation in the moving direction of the Doppler sample point.
Figure 21A:
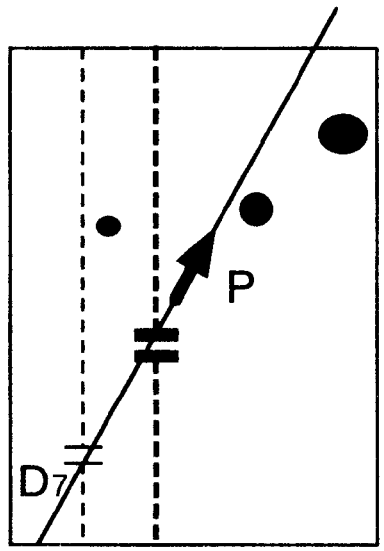
FIG. 21 is an explanatory view of the operation of FIG. 20.
Figure 21B:
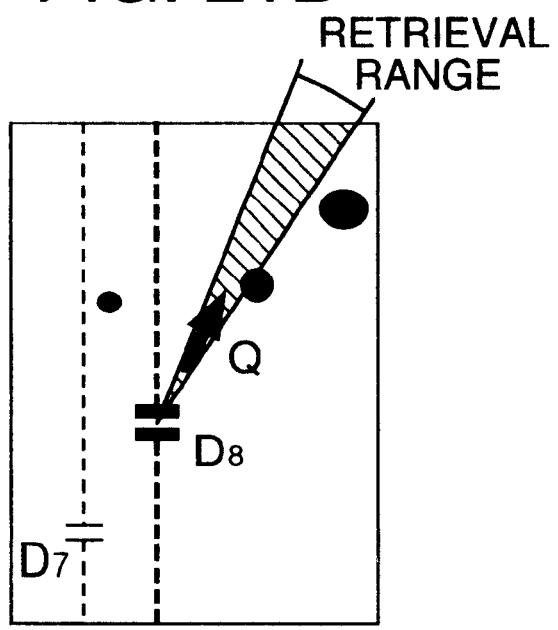

In FIG. 20, the steps 91 and 92 execute the same operation as the steps 81 and 82 in FIG. 18. Here, the blood stream portion is retrieved on the extension in the moving direction P of the Doppler sample point as shown in FIG. 21A. If the bloodstream portion exists, the flow jumps from the step 93 to the step 96 and the Doppler sample point is set. When the judgement result proves NO in the step 93, the bloodstream portion is retrieved in the step 94 from the next position $D_8$ by expanding the retrieving range by a predetermined range as represented by symbol Q as shown in FIG. 21B. If the judgement result proves YES in the step 95, the Doppler sample point is set in the step 96. If the result proves NO, the flow returns to the step 94, and the bloodstream portion is retrieved by further expanding the retrieving range by a predetermined range. Thereafter, the procedure is executed similarly.

In this way, retrieval of the Doppler sample point is executed semi-automatically, and the sample point can be set by detecting the fastest point in the step 96.

Figure 22:
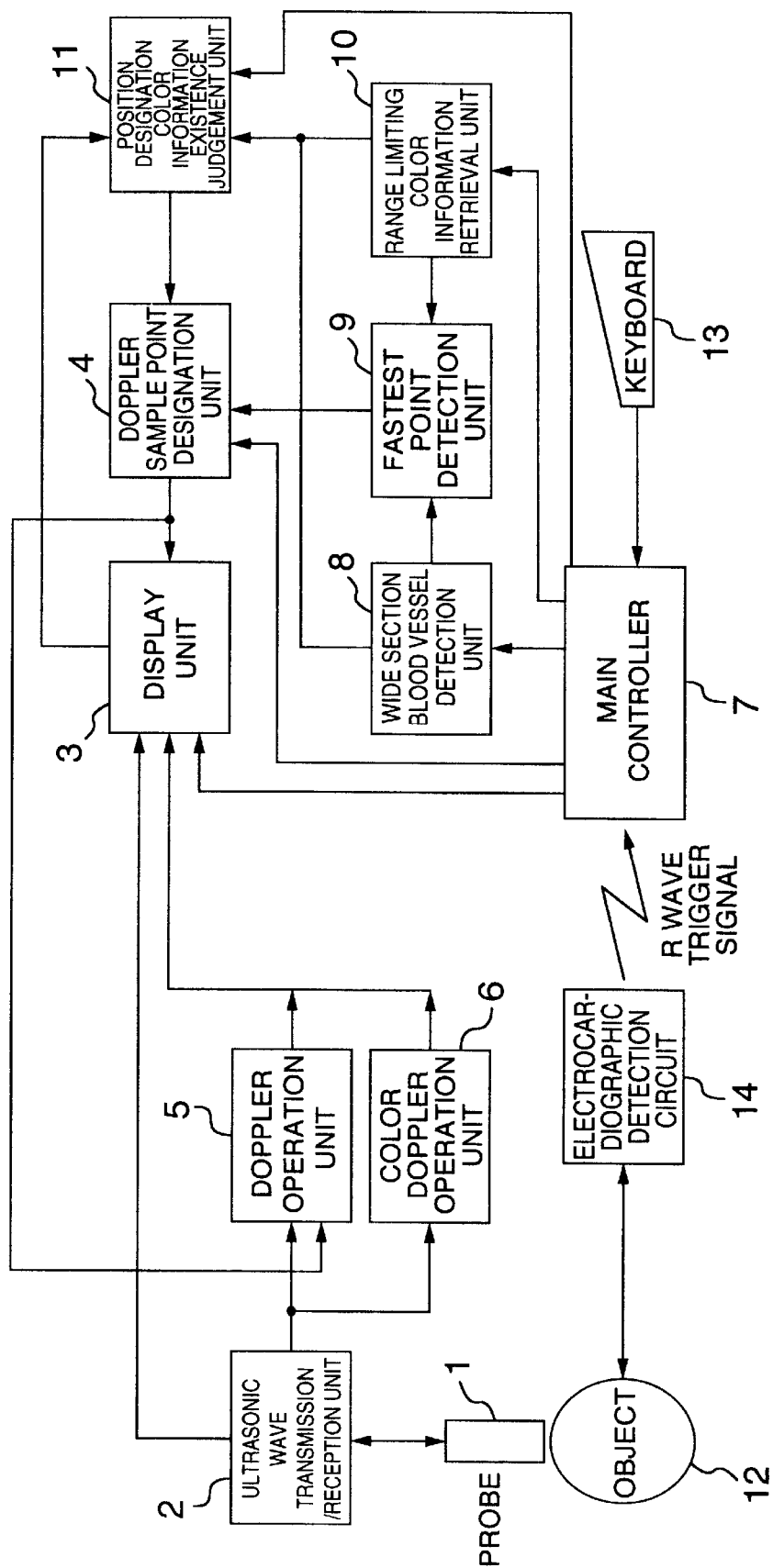
FIG. 22 is a block diagram of still another embodiment of the present invention.

FIG. 22 is a block diagram showing the ultrasonic tomograph according to further another embodiment of the present invention. In the ultrasonic tomograph of this embodiment, a position designating color information existence judgement unit 11 is further connected to the range limiting color information retrieval unit 10 of the ultrasonic tomograph shown in FIG. 17. This position designating color information existence judgement unit 11 functions as position designating bloodstream detection means for detecting the color bloodstream information at each moving position whenever the Doppler sample point is moved. This unit 11 is used in the case where the Doppler sample point is moved manually, and is moved automatically to the maximum velocity portion only when the color bloodstream information is hit.

Figure 23:
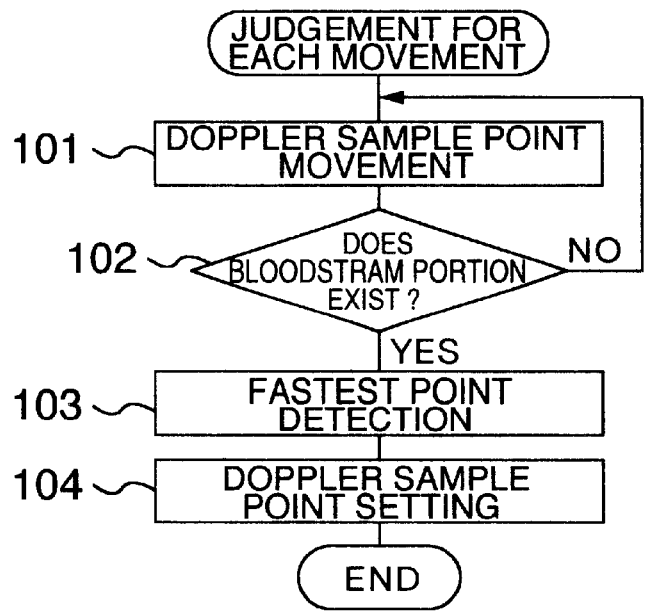
FIG. 23 is a flowchart showing the operation for judging the presence of the bloodstream portion for each movement.

FIG. 23 shows the operation flow of the position designating color information existence judgement unit 11 in this case.

Figure 24:
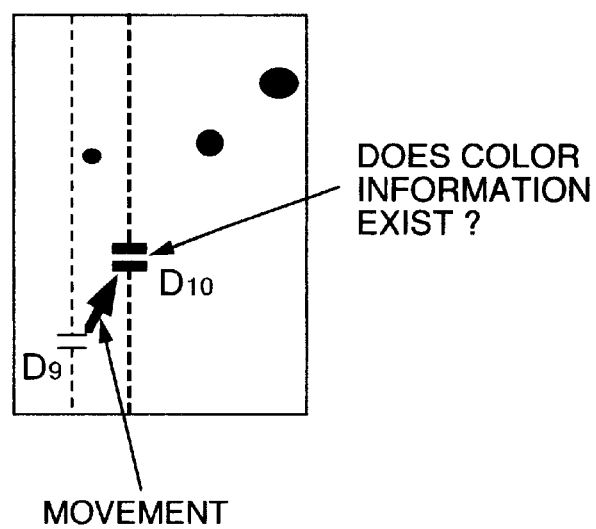
FIG. 24 is an explanatory view of the operation of FIG. 24.

In FIG. 23, whether or not the color bloodstream information exists on the Doppler sample point is judged whenever the Doppler sample point is moved manually in the steps 101 and 102. As shown in FIG. 24, whenever the Doppler sample point is moved to the position $D_9$, $D_{10}$ and so on, whether or not the color bloodstream information exists is judged at such positions $D_9$, $D_{10}$ in the step 102. When the color bloodstream information exists at such a position, the fastest point detection unit 9 is operated in the step 103. The Doppler sample point designation unit 4 automatically designates the Doppler sample point in the step 104. In this case, the Doppler sample point is moved manually, and when the color bloodstream information portion is hit, the Doppler sample point can be designated automatically to the highest flow velocity portion inside the color bloodstream information portion.

What is claimed is:

1. An ultrasonic tomograph for setting a Doppler sample point from bloodstream information, comprising:
   a probe for transmitting and receiving ultrasonic waves to and from an object;
   a signal processing unit for driving said probe to transmit the ultrasonic waves, receiving the ultrasonic reflected echo signals received by said probe, processing said signals and outputting an ultrasonic tomogram, a bloodstream image and bloodstream information;
   a display unit for displaying said ultrasonic tomogram, said bloodstream image and at least one Doppler sample point; and
   a control unit for at least one of semi-automatically and automatically setting the position of said at least one Doppler sample point on the basis of said bloodstream information which is data representing existence and flow velocity of the bloodstream for each pixel.

2. An ultrasonic tomograph according to claim 1, wherein said control unit sets the pixel having the highest flow velocity of said bloodstream as said at least one Doppler sample point.

3. An ultrasonic tomograph according to claim 1, wherein said control unit includes means for detecting a bloodstream portion comprising continuation of pixels, in which said bloodstream information exists, when said at least one Doppler sample point is moved to the existing position of said bloodstream information, means for retrieving said pixel having the highest bloodstream flow velocity data in said bloodstream portion, and means for setting said pixel retrieved by said retrieval means as said at least one Doppler sample point.

4. An ultrasonic tomograph according to claim 1, which further comprises a detection circuit for detecting living body signals from said object, and wherein said signal processing unit detects said bloodstream image and said bloodstream information for only a specific time phase on the basis of said living body signals.

5. An ultrasonic tomograph according to claim 4, wherein said living body signal is an electrocardiogram.

6. An ultrasonic tomograph according to claim 1, wherein said control unit includes means for defining a predetermined range inside the image displayed by said display unit, and means for setting said at least one Doppler sample point on the basis of said bloodstream information inside said range defined by said definition means.

7. An ultrasonic tomograph according to claim 1, which further comprises a Doppler operation unit for converting said bloodstream information to a color tone, and wherein said control unit sets said at least one Doppler sample point on the basis of said color tone converted by said Doppler operation unit.

8. An ultrasonic tomograph according to claim 1, wherein said control unit includes initial setting means for setting an initial position of said at least one Doppler sample point on the basis of said bloodstream information, and at least one Doppler sample point moving means for moving said at least one Doppler sample point.

9. An ultrasonic tomograph according to claim 8, wherein said Doppler sample point moving means includes moving direction detection means for detecting the moving direction when the movement of said at least one Doppler sample point is started, means for retrieving the existence of said pixels having said bloodstream information in a direction of a substantial extension of the moving direction detected by said moving direction detection means, and means for setting said pixel retrieved by said pixel retrieval means as said at least one Doppler sample point.

10. An ultrasonic tomograph according to claim 8, wherein said Doppler sample point moving means moves said at least one Doppler sample point under a condition different from the condition under which said initial setting means sets said at least one Doppler sample point.

11. An ultrasonic tomograph for setting at least Doppler sample point from bloodstream information, comprising:
   a probe for transmitting and receiving ultrasonic waves to and from an object;
   a signal processing unit for driving said probe to transmit the ultrasonic waves, receiving the ultrasonic reflected echo signals received by said probe, processing said signals and outputting an ultrasonic tomogram, a bloodstream image and bloodstream information;
   a display unit for displaying said ultrasonic tomogram, said bloodstream image and at least one Doppler sample point; and
   a control unit for setting the position of said at least one Doppler sample point on the basis of said bloodstream information;
   wherein said bloodstream information is data representing the existence of the bloodstream for each pixel, and wherein said control unit includes;
      bloodstream portion detection means for detecting at least one bloodstream mass as said bloodstream portion on the basis of said bloodstream information; and
      means for setting one of said bloodstream portions as said at least one Doppler sample point.

12. An ultrasonic tomograph according to claim 11, wherein said bloodstream portion detection means is means for defining said bloodstream portion by a profile of a closed curve connecting pixels at which said bloodstream exists to pixels at which said bloodstream does not exist.

13. An ultrasonic tomograph according to claim 12, wherein said bloodstream portion detection means includes means for deciding the size of each of said bloodstream portions.

14. An ultrasonic tomograph according to claim 13, wherein said size decision means counts the number of pixels inside the range encompassed by said profile, and expresses the size of said bloodstream portion by the count value so obtained.

15. An ultrasonic tomograph according to claim 14, which further comprises means for omitting said bloodstream portions having said count value smaller than a predetermined value.

16. An ultrasonic tomograph according to claim 14, which further comprises sequencing means for sequencing said bloodstream portions in accordance with the size decided by said size decision means.

17. An ultrasonic tomograph according to claim 16, which further comprises means for updating setting of said Doppler sample point in the sequence decided by said sequencing means.

18. An ultrasonic tomograph according to claim 13, wherein said Doppler sample point setting means sets the greatest bloodstream portion among said bloodstream portions decided by said size decision means as said at least one Doppler sample point.

19. An ultrasonic tomograph according to claim 11, wherein said bloodstream information contains data representing a flow velocity of said bloodstream for each pixel, and said Doppler sample point setting means is means for setting the pixel having the highest flow velocity of said bloodstream in said bloodstream portions set by said setting means, as said at least one Doppler sample point.

20. An ultrasonic tomograph according to claim 11 wherein said blood stream information contains data representing a flow velocity of said bloodstream for each pixel, and said Doppler sample point setting means includes the fastest point decision means for deciding said pixel having the highest flow velocity of said bloodstream in said bloodstream portions for each of said bloodstream portions when a plurality of said bloodstream portions exist, and means for setting said pixel having the highest flow velocity among the fastest points as said at least one Doppler sample point.

21. An ultrasonic tomograph according to claim 20, wherein said Doppler sample point setting means further includes velocity sequencing means for sequencing said fastest points in accordance with the higher velocity, and means for updating setting of said at least one Doppler sample point in the sequence sequenced by said sequencing means.

22. An ultrasonic tomograph for setting at least one Doppler sample point from bloodstream information, comprising:
   a probe for transmitting and receiving ultrasonic waves to and from an object;
   a signal processing unit for driving said probe to transmit the ultrasonic waves, receiving the ultrasonic reflected echo signals received by said probe, processing said signals and outputting an ultrasonic tomogram, a bloodstream image and bloodstream information;
   a display unit for displaying said ultrasonic tomogram, said bloodstream image and at least one Doppler sample point; and
   a control unit for setting the position of said at least one Doppler sample point on the basis of said bloodstream information;
   wherein said bloodstream information contains bloodstream flow velocity data for each pixel, and said control unit includes:
      bloodstream portion detection means for retrieving the existence of bloodstream information in a pixel unit from one of the ends of a screen, and detecting a mass of pixels having continuous bloodstream information as said bloodstream portion when said bloodstream information is retrieved;
      means for setting said pixel having the highest bloodstream flow velocity data in said bloodstream portions detected by said bloodstream portion detection means, as said at least one Doppler sample point; and
      means for retrieving the bloodstream information for pixels other than pixels of said bloodstream portion from the position of said set bloodstream portion when update command of said at least one Doppler sample point is given, and detecting a mass of pixels having continuous bloodstream information as said bloodstream portion.

23. A ultrasonic tomograph for setting at least one Doppler sample point from bloodstream information, comprising:
   a probe for transmitting and receiving ultrasonic waves to and from an object;
   a signal processing unit for driving said Probe to transmit the ultrasonic waves, receiving the ultrasonic reflected echo signals received by said probe, processing said signals and outputting an ultrasonic tomogram, a bloodstream image and bloodstream information;
   a display unit for displaying said ultrasonic tomogram, said bloodstream image and at least one Doppler sample point; and
   a control unit for setting the position of said at least one Doppler sample point on the basis of said bloodstream information;
   which further comprises a detection circuit for detecting living body signals from said object, and wherein said signal processing unit detects said bloodstream image and said bloodstream information for only a specific time phase on the basis of said living body signals;
   wherein said bloodstream information contains bloodstream flow velocity data, and said control unit includes bloodstream portion detection means for detecting a mass of bloodstreams as a bloodstream portion on the basis of said bloodstream information, and means for setting said pixel having the highest bloodstream flow velocity in said bloodstream portions as said at least one Doppler sample point.

24. An ultrasonic tomograph according to claim 23, wherein said Doppler sample point setting means retrieves a plurality of times said highest bloodstream flow velocity pixels, and sets the averaged position of a plurality of said highest bloodstream flow velocity pixels as said at least one Doppler sample point.

25. An ultrasonic tomograph for setting at least one Doppler sample point from bloodstream information, comprising:
   a probe for transmitting and receiving ultrasonic waves to and from an object;
   a signal processing unit for driving said probe to transmit the ultrasonic waves, receiving the ultrasonic reflected echo signals received by said probe, processing said signals and outputting an ultrasonic tomogram, a bloodstream image and bloodstream information;
   a display unit for displaying said ultrasonic tomogram, said bloodstream image and at least one Doppler sample point; and
   a control unit for setting the position of said at least one Doppler sample point on the basis of said bloodstream information;
   wherein said control unit includes initial setting means for setting an initial position of said at least one Doppler sample point on the basis of said bloodstream information, and at least one Doppler sample point moving means for moving said Doppler sample point; and
   wherein said Doppler sample point moving means includes moving direction detection means for detecting the moving direction when the movement of said at least one Doppler sample point is started, means for retrieving the existence of said pixels having said bloodstream information in a range expanded much more than the extension of the moving direction detected by said moving direction detection means, and means for setting said pixel retrieved by said pixel retrieval means as said at least one Doppler sample point.

26. An ultrasonic tomograph according to claim 25, wherein said retrieval means expands said retrieval range in accordance with the increase of the moving distance of said at least one Doppler sample point.

27. An ultrasonic tomograph for setting at least one Doppler sample point from bloodstream information, comprising:
   a probe for transmitting and receiving ultrasonic waves to and from an object;
   a signal processing unit for driving said probe to transmit the ultrasonic waves, receiving the ultrasonic reflected echo signals received by said probe, processing said signals and outputting an ultrasonic tomogram, a bloodstream image and bloodstream information;

a display unit for displaying said ultrasonic tomogram, said bloodstream image and at least one Doppler sample point; and a control unit for setting the position of said at least one Doppler sample point on the basis of said bloodstream information;

wherein said control unit includes initial setting means for setting an initial position of said at least one Doppler sample point on the basis of said bloodstream information, and at least one Doppler sample point moving means for moving said at least one Doppler sample point; and wherein said Doppler point moving means includes means for judging whether or not said bloodstream information exists in said pixel moved afresh when the movement of said at least one Doppler sample point is started, and means for setting said pixel as said at least one Doppler sample point when said judgement means judges said bloodstream information as existing.

28. A method of setting at least one Doppler sample point in an ultrasonic diagnostic apparatus comprising the steps of:

generating transmission signals for transmitting ultrasonic waves to an object;

generating reception signals by the ultrasonic waves reflected from said object;

forming an ultrasonic tomogram on the basis of said transmission signals and said reception signals, and forming a bloodstream image containing bloodstream information;

displaying said ultrasonic tomogram and said bloodstream image together with said at least one Doppler sample point; and at least one of semi-automatically and automatically setting a display position of said at least one Doppler sample point on the basis of said bloodstream information which is data representing existence and flow velocity of the bloodstream for each pixel.

* * * * *